(12) United States Patent
   Tinker (10) Patent No.: US 8,021,422 B2
(45) Date of Patent: *Sep. 20, 2011

(54) ACTUATING MECHANISM FOR PNEUMATICALLY-DRIVEN ARTIFICIAL HEART

(75) Inventor: Frank A. Tinker, Tucson, AZ (US)

(73) Assignee: Syncardia Systems, Inc., Tucson, AZ (US)

( * ) Notice: Subject to any disclaimer, the term of this patent is extended or adjusted under 35 U.S.C. 154(b) by 185 days.

This patent is subject to a terminal disclaimer.

(21) Appl. No.: 12/454,440

(22) Filed: May 18, 2009

(65) Prior Publication Data

US 2010/0292786 A1    Nov. 18, 2010

(51) Int. Cl.
  *A61M 1/10*   (2006.01)
(52) U.S. Cl. .................................................... 623/3.1
(58) Field of Classification Search .......... 623/3.1–3.21; 600/16
  See application file for complete search history.

(56) References Cited

U.S. PATENT DOCUMENTS

| | | | |
|---|---|---|---|
| 3,636,570 A * | 1/1972 | Nielson | 623/3.24 |
| 4,611,578 A | 9/1986 | Heimes | |
| 5,766,207 A | 6/1998 | Potter et al. | |
| 2006/0129024 A1* | 6/2006 | Weatherbee | 600/16 |
| 2008/0064917 A1* | 3/2008 | Bar et al. | 600/16 |
| 2009/0270981 A1* | 10/2009 | Yavorski et al. | 623/3.21 |

* cited by examiner

*Primary Examiner* — Suzette J Gherbi
(74) *Attorney, Agent, or Firm* — Antonio R. Durando (57) ABSTRACT

A pneumatic pump comprises two coaxial cylindrical pumping chambers, each enclosing a piston connected to the other through a partition by a tube, thereby forming a monolithic piston assembly that is driven axially by a common electrical actuator providing reciprocating motion. The volume in the bottom chamber is selected as needed to provide the desired pressure in the left ventricle of an artificial heart driven by the pump. The diameter of the tube connecting the pistons is selected such that the stroke volume of the top chamber is reduced with respect to that of the bottom chamber as needed to match the reduced pressure requirements of the right ventricle of the artificial heart. Check valves are used in each chamber to ensure venting of excess pressure during the blood ejection phase and to limit the vacuum during the fill phase.

19 Claims, 7 Drawing Sheets

FIG. 3   AIR LINE CONNECTS THROUGH SKIN TO POWER CONSOLE

ACTUATING MECHANISM FOR PNEUMATICALLY-DRIVEN ARTIFICIAL HEART

BACKGROUND OF THE INVENTION

1. Field of the Invention

The invention relates to a portable mechanism for actuating a pneumatically-driven artificial heart.

2. Description of the Prior Art

The heart is the muscle that drives the cardiovascular system in living beings. Acting as a pump, the heart moves blood throughout the body to provide oxygen, nutrients, hormones, and to remove waste products. The blood follows two separate pathways in the human body, the so-called pulmonary and systemic circulatory circuits. In the pulmonary circuit, the heart pumps blood first to the lungs to release carbon dioxide and bind oxygen, and then back to the heart. Thus, oxygenated blood is constantly being supplied to the heart. In the systemic circuit, the longer of the two, the heart pumps oxygenated blood through the rest of the body to supply oxygen and remove carbon dioxide, the byproduct of metabolic functions carried out throughout the body. The heart supplies blood to the two circuits with pulses generated by the orderly muscular contraction of its walls.

Figure 1:
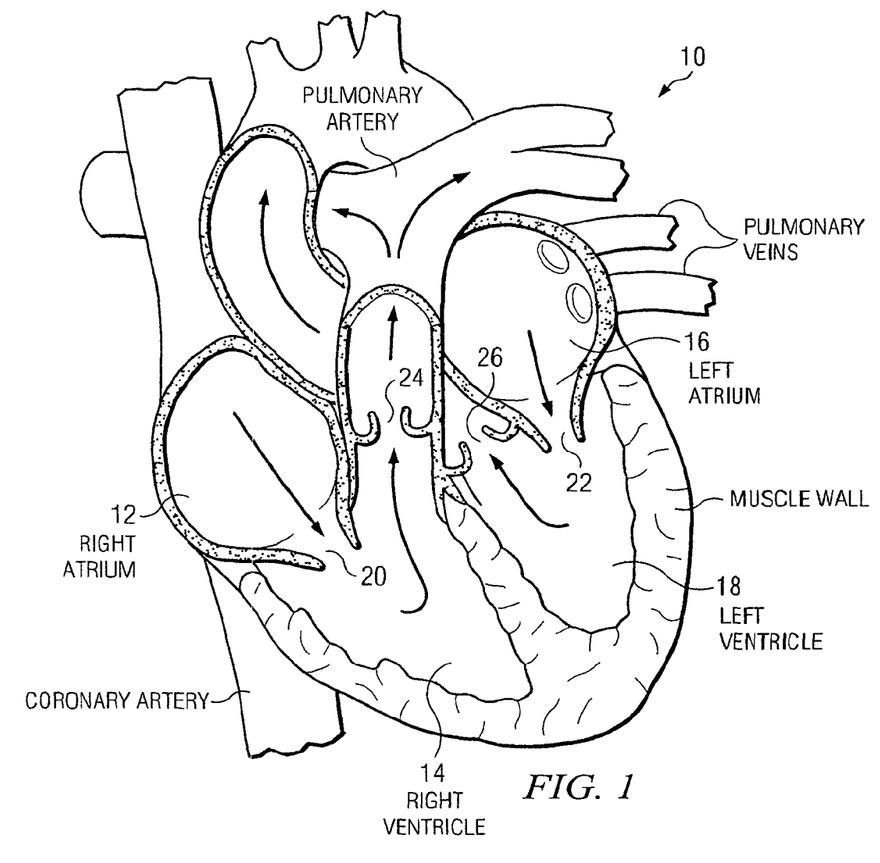
FIG. 1 is a representation of a human heart.

In order to keep blood moving through these two separate circulatory circuits, the human heart has four distinct chambers that work in pairs. As illustrated in FIG. 1, the heart 10 includes a right atrium 12, a right ventricle 14, a left atrium 16, and a left ventricle 18. One pair of chambers, the right ventricle and left atrium, is connected directly to the pulmonary circuit. In it, de-oxygenated blood from the body is pumped from the right ventricle 14 to the lungs, where it is oxygenated, and then back to the left atrium 16.

In the systemic circuit, the other pair of chambers pumps the oxygenated blood through body organs, tissues and bones. The blood moves from the left atrium 16, where it flows from the lungs, to the left ventricle 18, which in turn pumps the blood throughout the body and all the way back to the right atrium 12. The blood then moves to the right ventricle 14 where the cycle is repeated. In each circuit, the blood enters the heart through an atrium and leaves the heart through a ventricle.

Thus, the ventricles 14,18 are essentially two separate pumps that work together to move the blood through the two circulatory circuits. Four check valves control the flow of blood within the heart and prevent flow in the wrong direction. A tricuspid valve 20 controls the blood flowing from the right atrium 12 into the right ventricle 14. Similarly, a bicuspid valve 22 controls the blood flowing from the left atrium 16 into the left ventricle 18. Two semilunar valves (pulmonary 24 and aortic 26) control the blood flow leaving the heart toward the pulmonary and systemic circuits, respectively. Thus, in each complete cycle, the blood is pumped by the right ventricle 14 through the pulmonary semilunar valve 24 to the lungs and back to the left atrium 16. The blood then flows through the bicuspid valve 22 to the left ventricle 18, which in turn pumps it through the aortic semilunar valve 26 throughout the body and back to the right atrium 12. Finally, the blood flows back to the right ventricle 14 through the tricuspid valve 20 and the cycle is repeated.

When the heart muscle squeezes each ventricle, it acts as a pump that exerts pressure on the blood, thereby pushing it out of the heart and through the body. The blood pressure, an indicator of heart function, is measured when the heart muscle contracts as well as when it relaxes. The so-called systolic pressure is the maximum pressure exerted by the blood on the arterial walls when the left ventricle of the heart contracts forcing blood through the arteries in the systemic circulatory circuit. The so-called diastolic pressure is the lowest pressure on the blood vessel walls when the left ventricle relaxes and refills with blood. Healthy blood pressure is considered to be about 120 millimeters of mercury systolic and 80 millimeters of mercury diastolic (usually presented as $^{120}/_{80}$).

Inasmuch as the function of the circulatory system is to service the biological needs of all body tissues (i.e., to transport nutrients to the tissues, transport waste products away, distribute hormones from one part of the body to another, and, in general, to maintain an appropriate environment for optimal function and survival of tissue cells), the rate at which blood is circulated by the heart is a critical aspect of its function. The heart has a built-in mechanism (the so-called Frank-Starling mechanism) that allows it to pump automatically whatever amount of blood flows into it. Such cardiac output in a healthy human body may vary from about 4 to about 15 liters per minute (LPM), according to the activity being undertaken by the person, at a heart rate that can vary from about 50 to about 180 beats per minute.

Several artificial devices have been developed over the years to supplement or replace the function of a failing heart in patients. These include devices developed by companies as well as research institutions such as the Berlin Heart Institute, the Pennsylvania State University, the University of Utah, the Cleveland Clinic Foundation, the University of Perkinje (in Bruno, Czechoslovakia), the University of Tokyo, the Thoratec Corporation, Abiomed Inc., Novacor, and Symbion Inc. Typically, these artificial devices consist of pumps that aim at duplicating the required pumping functions of the left and right human ventricles. One method of actuation for these pumps has been through the pneumatic action of an external mechanism. See, for example, U.S. Pat. Nos. 4,611,578 and 5,766,207. Periodic pulses of compressed air drive the pumps at the desired pressure and rate of cardiac output. A moderate vacuum may be applied between pulses to allow more rapid refilling of the ventricles with blood flowing from the respective atrium.

Figure 2:
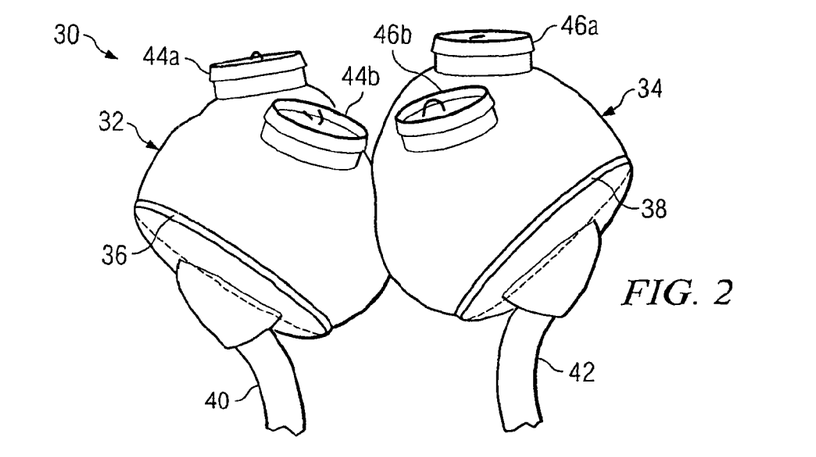
FIG. 2 is a schematic view of the SynCardia artificial heart for which the present invention has been developed.
Figure 3:
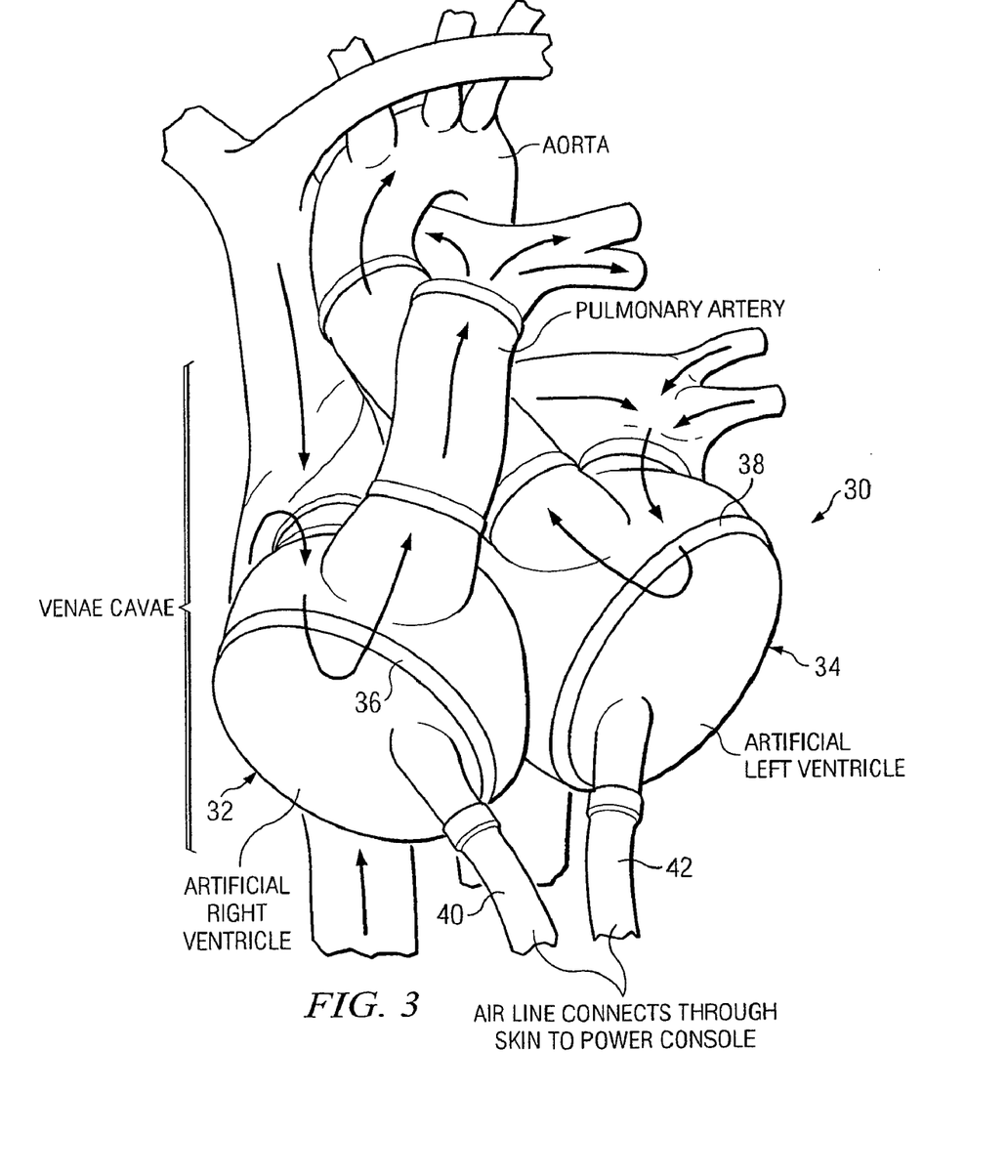
FIG. 3 is a representation of the artificial heart of FIG. 2 connected to the heart atria of a human body.

One notable artificial heart currently in use as an implant for patients waiting for a heart transplant is the Total Artificial Heart manufactured by SynCardia Systems, Inc., of Tucson, Ariz. Designed to operate much the same way as a human heart, this artificial heart replaces the two active chambers (i.e., the ventricles) of the human heart with corresponding artificial components. As illustrated in FIG. 2, such artificial heart 30 includes two separate chambers or ventricles 32 and 34 that replace the right and left ventricles of the human heart, respectively. Each chamber is equipped with a respective diaphragm (36 and 38 in the right and left chamber, respectively) that has an air contact side and a blood contact side. Each diaphragm is designed as a spherical hemisphere. As shown in FIG. 3, the artificial heart 30 is implanted by connecting the top of the right chamber 32 to the right atrium 12 and the top of the left chamber 34 to the left atrium 16. The bottom of each chamber is provided with an air line (40 and 42 in the right and left chamber, respectively) that is embedded in the patient's body but extends outside for connection to a pneumatic driver.

When driven by a supply of pressurized air from the pneumatic driver, each diaphragm 36,38 discharges blood from the respective chamber 32,34 simulating the function of a ventricle. This phase is referred to in the art as systole or equivalently as the ejection phase. When the pressurized air is removed from the diaphragm, known as diastole or the filling phase, blood can enter the ventricle from the connected atrium. The rate at which blood enters the ventricle depends on the difference between the atrial pressure and the pressure on the air-side of the diaphragm. To increase this filling rate, a slight vacuum of about 10 mmHg is normally applied to the air-side of the diaphragm during diastole. Artificial valves $44a$ (tricuspid), $46a$ (bicuspid) and $44b$ (pulmonary), $46b$ (aortic) control the flow from the respective atrium into each artificial ventricle and out to the circulatory systems, respectively.

The pneumatic drivers used to date for driving all artificial hearts have been cumbersome and inadequate for affording patients any degree of independent mobility. They employ compressors, vacuum pumps, and air tanks coupled to electrically actuated valves, all of which amounts to a large and heavy apparatus that can only be transported on wheels and with considerable effort. Therefore, many attempts have been made during the last two decades to produce a portable driver for these devices. However, because of the complexity of the required functionality and the hardware necessary to produce it, pneumatic heart drivers continue to be bulky, require frequent maintenance, and often provide air pulses that do not match the performance of the larger drivers they are meant to replace. Even at the approximate weight of 20 pounds and size of about 0.7 cubic feet achieved so far, pneumatic drivers remain unwieldy and substantially not portable for a patient who is kept alive by an artificial heart.

In essence, a portable driver needs to be reliable, durable, easy to use, and sufficiently simple in design to be affordable. Unfortunately, each of these requirements contributes to the complexity of the design, which in turn has produced devices that are not sufficiently small and light-weight to be manageable in the hands of a patient. Furthermore, it is essential that the pneumatic driver be able to provide the correct pressure balance between the left and right ventricles of the artificial heart to ensure the proper operating pressure to the pulmonary and systemic circuits regardless of the speed of operation. Typically, this requires that the driver be able to operate so as maintain, on average, a right atrial pressure of about 9 mmHg, a mean pulmonary artery pressure of about 35 mmHg, a left atrial pressure of about 10 mmHg, and a mean aortic pressure of about 95 mmHg.

This need to provide different operating pressures to the right and left chambers (ventricles) of the artificial-heart device has not been met heretofore with a simple design suitable for a portable driver. For example, the blood pump described in U.S. Pat. No. 4,611,578 includes a configuration wherein two reciprocating pistons in a common cylinder may be operated alternatively to provide redundancy or independently to actuate two separate pneumatically driven blood pumps. This issue is not addressed in the patent, but it describes a sophisticated control system that arguably could be used to provide the correct operating pressure to each chamber of the artificial heart. However, the complex and multi-component structure of the device necessarily requires a relatively heavy and large apparatus, though described as portable. The commercially available module weighs about 25 pounds and is approximately 0.6 cubic feet in volume.

U.S. Pat. No. 5,766,207 describes another portable pneumatic driver for ventricular assist devices that could also be adapted for an artificial heart. The single pump of the invention could be used to drive both ventricles of an artificial heart, but only at the same pressure and volume rate. Thus, this device, even if modified to meet the other requirements of a portable artificial-heart driver, would not be suitable as an alternative to the stationary modules currently in use.

Therefore, there remains a strong need for an artificial-heart pneumatic driver that provides the detailed functions of stationary modules, is highly reliable, light-weight and manageable in size, so as to be easily portable for a patient in the normal condition of a person in need of a heart transplant. The present invention provides an extremely simple and elegant solution to this problem in a configuration designed particularly to meet the specifications of the SynCardia artificial heart.

SUMMARY OF THE INVENTION

The major concerns in designing a portable driver relate to size, weight, reliability, durability, extended battery life, ease of use, and simplicity of design (which in turn affects cost). With these constraints in mind, the present invention is directed at providing coordinated and independent periodic actuation pressure to each ventricle of the artificial heart, limiting peak pressures and peak vacuums to provide a safe and efficient cycle of operation, allowing only partial filling of each ventricle of the cardiac device to ensure redundancy of capacity, providing sufficient pneumatic stroke to completely eject the blood from the ventricles at each beat, readily adjusting the rate at which the artificial heart is actuated, and minimizing overall size and weight to enable portability.

In view of the foregoing, the preferred embodiment of the pump of the invention comprises two coaxial cylindrical pumping chambers, each enclosing a disk-shaped piston incorporating seals to eliminate leakage. The pistons are connected to one another through a partition by a tube, thereby forming a monolithic piston assembly that is driven axially by a common electrical actuator providing reciprocating motion through a rod connected to the top piston. The tube travels through a seal in the partition that separates the two chambers and, by defining the boundary between the pistons, also acts as a bulkhead for the top chamber.

The volume in the bottom chamber is selected as needed to provide the desired pressure in the left ventricle of the artificial heart driven by the pump. According to one aspect of the invention, the diameter of the tube connecting the pistons is selected such that the stroke volume (i.e., the displacement) of the top chamber is reduced with respect to that of the bottom chamber as needed to match the reduced pressure requirements of the right ventricle of the artificial heart. Namely, the maximum pressure achieved in each chamber should be as needed to fully eject blood from each ventricle of the artificial heart substantially at the operating pressures of the human pulmonary and systemic circulatory circuits. A limit check valve is preferably used in each chamber to ensure venting of excess pressure during the compression stroke. A limit check valve is also preferably used in each chamber to limit the vacuum generated during the reverse, aspiration stroke.

In an alternative embodiment of the invention, the top and bottom pistons may have different diameters and travel with the same stroke length along cylindrical housings of correspondingly different volumes, thereby achieving the same effect of producing different pressures in the ventricles of the artificial heart. In a third embodiment, the height of one of the piston housings may be greater than the stroke length, so as to provide a buffer zone to reduce the operating pressure of that piston. The same result may be achieved with an external buffer zone that may consist of an additional chamber or in an additional volume in the air line to the artificial ventricle.

Additional features and advantages of the invention will be forthcoming from the following detailed description of certain specific embodiments when read in conjunction with the accompanying drawings.

DESCRIPTION OF THE PREFERRED EMBODIMENTS

Figure 4:
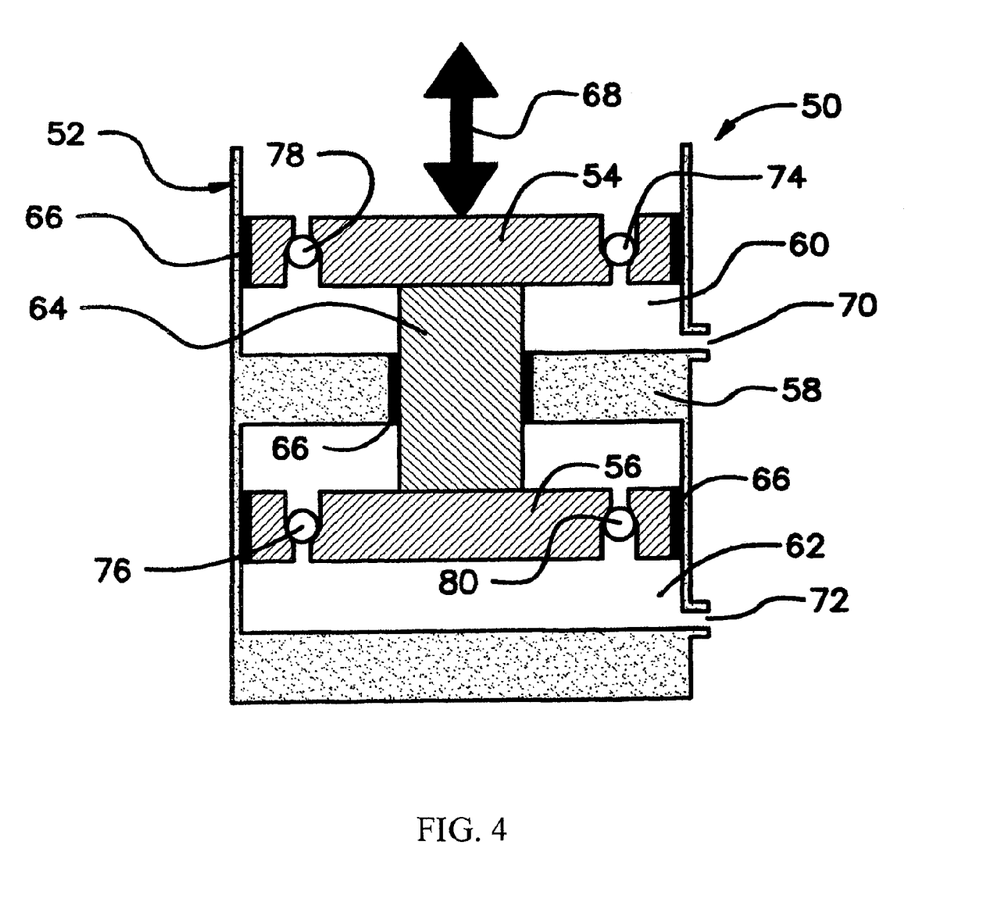
FIG. 4 is a schematic view of a pneumatic driver according to the preferred embodiment of the invention.

With reference to the schematic representation of FIG. 4, the preferred embodiment of a pneumatic pump 50 according to the invention includes a single cylinder housing 52 wherein two parallel pistons 54,56 are mounted for axial reciprocating motion. A partition or bulkhead 58 between the two pistons defines two separate pumping chambers or cylinders 60 and 62 for actuating, respectively, the right and left ventricles of the artificial heart driven by the pump 50. The pistons 54,56 are rigidly connected to one another by means of a rod or tube 64 that is slidably mounted through the partition 58. Seals 66 are provided on all sliding surfaces to prevent leakage. A piston actuator 68 is connected to one of the pistons for periodic reciprocating translation along the longitudinal axis of the cylinder 52.

For ease of description, the terms right and left are used in describing the pump 50 with reference to the right and left ventricles (or chambers) of the artificial heart to which the chambers 60,62 are connected. Similarly, the terms top or upper and bottom or lower are used to refer to the upper and lower chambers 60 and 62 and to their respective components, as illustrated in the figures, but it is understood that this relative position has not significance in relation to the invention. A driveline (seen in FIG. 6) connects the right drive port 70 of the upper chamber 60 to the air line 40 of the pneumatically-driven right ventricle of the artificial heart (see FIG. 3). Similarly, a separate driveline (also shown in FIG. 6) connects the left drive port 72 of the lower chamber 62 to the air line 42 of the pneumatically-driven left ventricle of the artificial heart.

As the piston assembly is pushed down by the actuator 68, the working gas in each of the upper and lower chambers 60,62 is exhausted through their respective ports 70,72 to pressurize and actuate the diaphragms 36,38 in the right and left ventricles of the artificial heart in the patient. The pressure exerted on each diaphragm forces blood to flow from the blood-side of the ventricles to the patient's body (the eject phase). The upper chamber 60 is equipped with a right-drive pressure relief valve 74 to ensure that air is expelled from the chamber if the right-drive pressure exceeds a predetermined level (the cracking pressure of the pressure relief valve), thereby providing a safety pressure limit. Similarly, air is expelled from lower chamber through a left-drive pressure relief valve 76 if the left-drive pressure exceeds the cracking pressure of the relief valve. Because the chambers operate at different maximum pressures, the cracking pressures of the relief valves are set at correspondingly different levels, typically at 103 mmHg and 212 mmHg for the right- and left-drive pressures, respectively.

As the piston assembly is pulled up by the reciprocating motion of the actuator 68, the working gas in each of the upper and lower chambers 60,62 is drawn back through their respective ports 70,72 and a vacuum (relative to atmospheric pressure) is generated to aid the reverse motion of the diaphragms 36,38 in the right and left ventricles of the artificial heart. The negative pressure exerted on each diaphragm creates a suction that helps the flow of blood from each atrium of the patient's heart to the blood-side of the ventricles of the artificial heart (the fill phase). In order to also ensure against excessive vacuum levels, the upper chamber is equipped with a right-drive vacuum relief valve 78 that allows air to be drawn from the atmosphere if the right-drive vacuum exceeds a predetermined level (the cracking pressure of the vacuum relief valve). Similarly, air is drawn into the lower chamber through a left-drive vacuum relief valve 80 if the left-drive vacuum exceeds the cracking pressure of the vacuum relief valve. These limiting cracking pressures are optimally set to achieve sufficient vacuum, namely about 10 mmHg, at each ventricle to ensure matching fill volumes.

According to a critical aspect of the invention, the diameter of the connecting tube 64 is sized so as to provide an output flow rate from the upper chamber 60 designed to match the pressure requirements of the right ventricle 32 of the artificial heart. Once the stroke and volume of the lower chamber 62 are set to provide the desired pressure to the left ventricle 34 of the artificial heart at the nominal rate of operation of the pump, the pressure provided by the upper chamber can be adjusted as necessary simply by calculating the diameter of the tube 64 that produces the output rate required for the target pressure. As one skilled in the art will readily understand, the maximum pressures exerted on the diaphragms 36,38 are a function of the overall changes in volume produced by the stroke of each piston 54,56. That is, if the total volume of the chamber, the artificial heart ventricle, and the air line connecting them is halved during a compression stroke under substantially isothermal conditions, the pressure will approximately double. Therefore, the sizing of the displacement in each chamber 60,62, including the diameter of the tube 60 according to the invention, to meet the pressure requirements of each ventricle 32,34 is a matter of simple calculation.

The reciprocating actuator 68 for the piston assembly of the invention is preferably based on a mechanism (detailed in a separate disclosure) that produces a sinusoidal motion of the pistons. Such rate of compression and aspiration has been found to produce the required pressure profiles during the compression stroke to completely empty each ventricle 32,34 of the blood accumulated during the aspiration stroke. Similarly, the vacuum generated during the aspiration stroke, together with the natural flow of blood from the atria, produces the required filling of the ventricles. Operation of the artificial heart is engineered such that the ventricles are only partially filled during normal conditions in order to provide redundant capacity when the blood flow in the body of the patient is increased as a result of physical activity.

Figure 6:
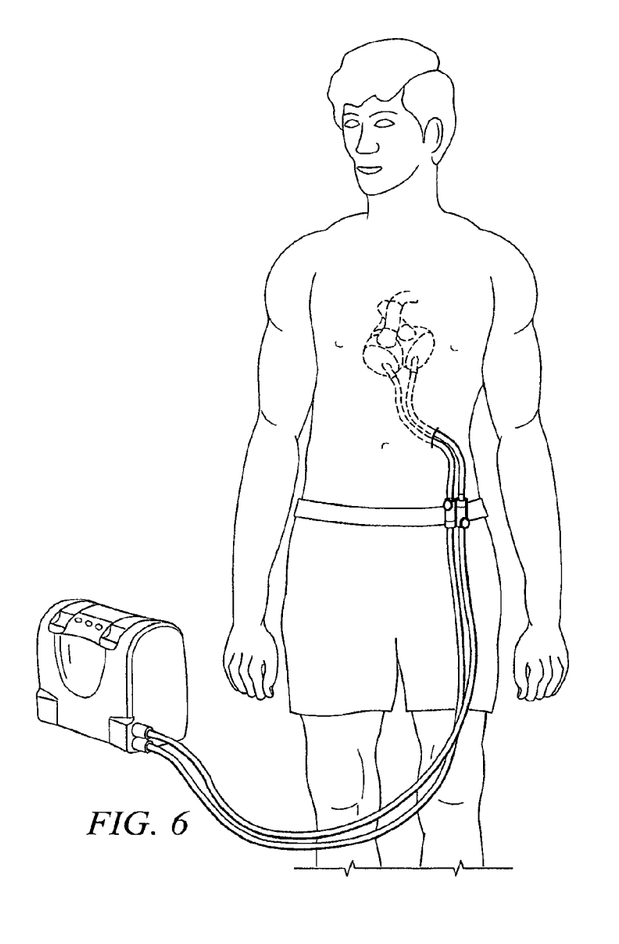
FIG. 6 is an illustration of the portable driver of the invention connected to an artificial heart implanted in a human body.

In the specific embodiment of the invention designed for the SynCardia artificial heart, the air side of each ventricle has a volume of approximately 4.27 cubic inches and the diaphragms 36,38 have an approximate area of 6.37 inch square each. The diameter and the stroke length of the pistons 54,56 are 3.0 and 0.943 inches, respectively, and the diameter of the tube 64 is 1.1 inches, producing displacements of 5.77 and 6.67 cubic inches in the upper and lower chambers 60,62, respectively. The total air volume of the pump chamber, the ventricle and the air line connecting them under uncompressed conditions is 16.51 and 17.41 cubic inches in the right and left ventricle systems, respectively. Operating at 125 cycles (beats) per minute, the pump of the invention produces operating pressures of 103 and 212 mmHg in the right and left ventricles, respectively, causing each ventricle to fill with about 55 cc of blood and completely ejecting it at each stroke. The compactness of the design of the pump of the invention, together with the novel reciprocating mechanism actuating it (described separately), has enabled the manufacture of a portable driver prototype weighing less than 12 pounds and sized like a small purse. FIG. 6 illustrates its size and portability as a patient's accessory.

Figure 7:
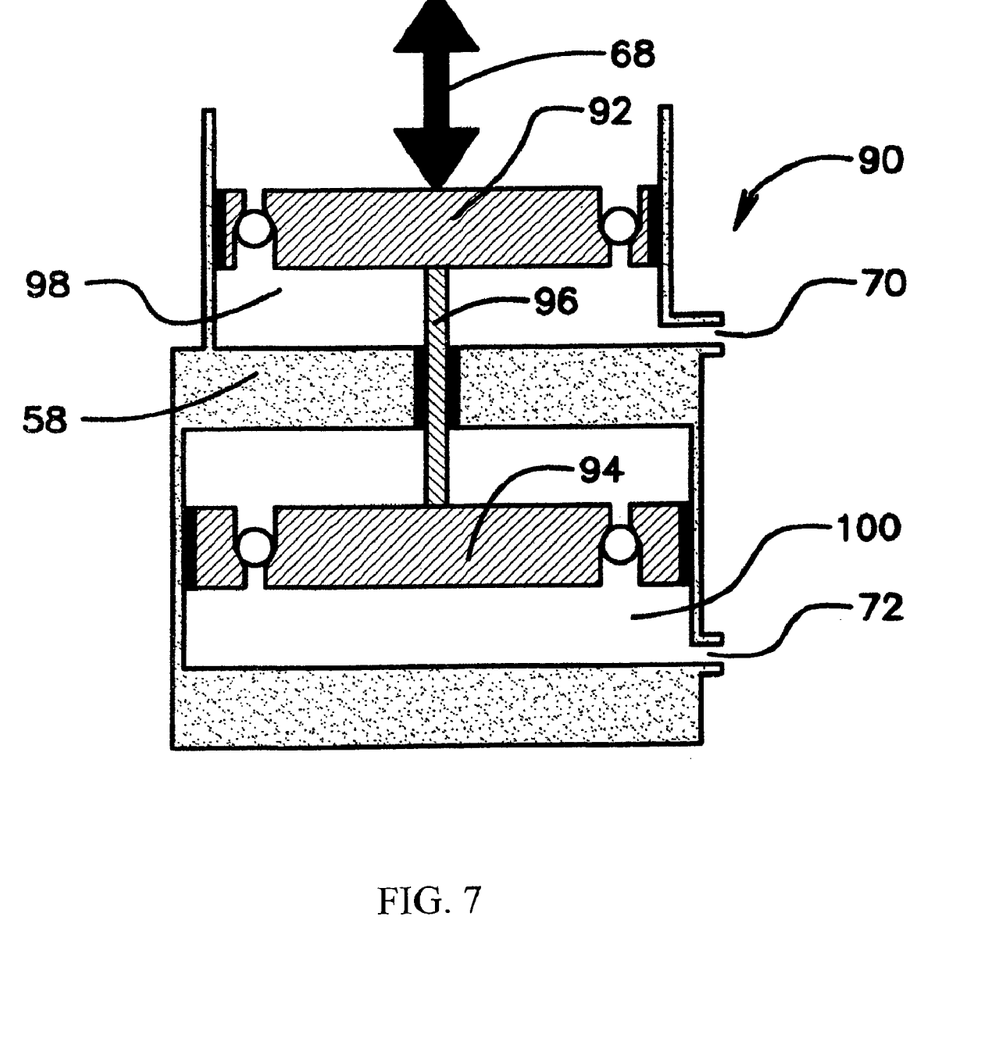
FIG. 7 is a view of an alternative embodiment of the invention wherein the pneumatic driver features a single housing with two piston/cylinder combinations of different diameter.

In a different embodiment 90 of the invention illustrated schematically in FIG. 7, two pistons 92,94 are also connected by a rod 96 through a partition 58 defining two separate cylinder chambers 98,100. The pistons are similarly actuated by a common reciprocating mechanism 68. However, the lower pressure in the upper (right ventricle) chamber 100 is obtained by decreasing its diameter and the corresponding displacement associated with each piston stroke.

Figure 8:
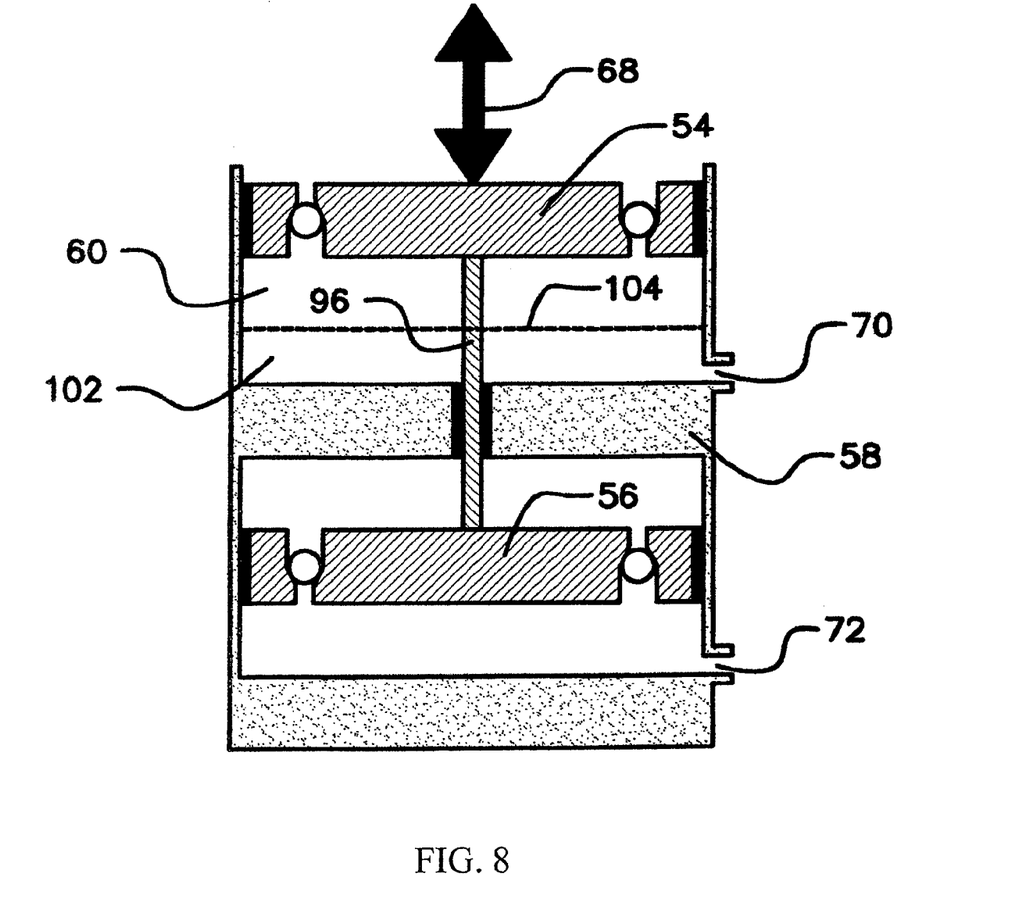
FIG. 8 is a view of a third embodiment wherein the upper-pressure cylinder incorporates a buffer zone to increase the working volume of gas compressed by that cylinder.
Figure 9:
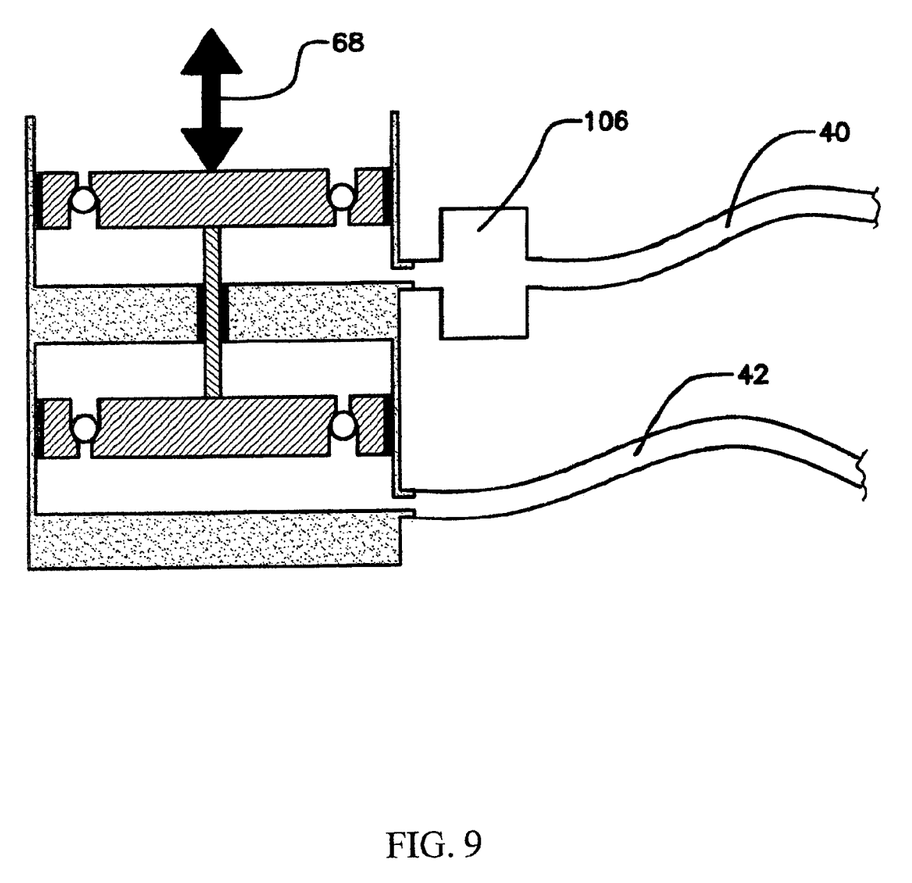
FIG. 9 is a view of another embodiment of the invention wherein the additional working volume is implemented with a buffer chamber connected to the upper-pressure cylinder.

The same result may be obtained with a housing of constant diameter, as in the pump 50 of FIG. 4, but with the upper chamber 60 lengthened beyond the stroke of the piston 54, thereby providing an additional cylinder volume 102, illustrated in FIG. 8 by the phantom line delineation 104. This additional volume provides a buffer zone that reduces the pressure exerted by the stroke of the piston 54. In an equivalent embodiment, illustrated in FIG. 9, this additional volume is provided by a buffer chamber 106 placed along the air line 40 to the low-pressure artificial ventricle 32. The same result could be achieved simply by sizing the lines 40 and 42 as necessary to provide the required volume difference for the two ventricle systems. As in the case of the preferred embodiment of the invention, the sizing of the relative dimensions of the various chambers and buffer volumes of these alternative embodiments are simply a matter of calculation based on the desired pressure delivered at each artificial ventricle.

Figure 5:
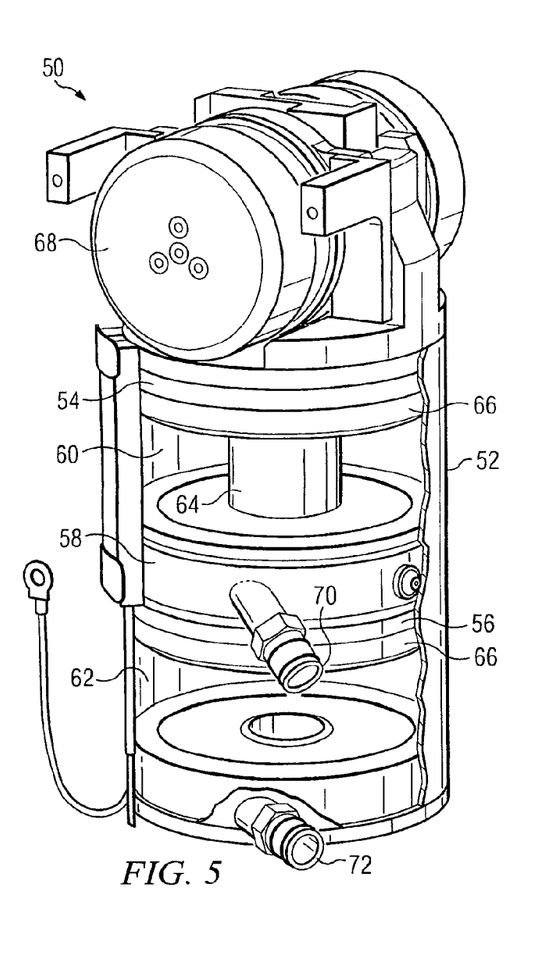
FIG. 5 is a sectioned view of the actual pneumatic driver that incorporates the concepts of the invention.

While the invention has been shown and described herein with reference to what is believed to be the most practical embodiment, it is recognized that departures can be made within the scope of the invention. For example, the pistons of the invention could be substituted with diaphragms connected by a tube or rod sized to produce the same effect described herein. Similarly, the cylindrical housing wherein the pistons are housed and the connecting tube need not be of circular cross-section, any shape being suitable so long as capable of producing the different pressures required for the operation of the right and left ventricle with the same stroke of the pistons. Further, a single valve that performs both pressure and vacuum limiting functions could be used. Such a valve could be a force-actuated valve that opened and closed as required by the system either through electrical means or as a function of a mechanical connection between the valve and the piston actuator. The pressure relief valve could also be implemented as a seal-break feature in the cylinder that would allow air to bypass the air seal between the piston and the cylinder wall at a predetermined point in the stroke. The pressure and vacuum limiting valves can also be placed in the chamber boundaries, as seen in FIG. 5, rather than in the pistons.

I claim:

1. A pump for driving an artificial heart comprising a right ventricle and a left ventricle actuated by pneumatic pressure, comprising:

a housing;
a pair of pistons slidably mounted inside the housing;
a partition defining two separate chambers in the housing, each chamber containing one of said pistons;
a connector coupling said pair of pistons through the partition; and
a port connecting each of said chambers to a respective ventricle of the artificial heart;
wherein said separate chambers are adapted to produce respective displacements such that a maximum pressure produced by a stroke of the pump in the right ventricle is a predetermined fraction of a maximum pressure produced by said stroke in the left ventricle of the artificial heart.

2. The pump of claim 1, wherein said separate chambers and respective pistons are substantially equal in cross-section and said connector is sized such that said maximum pressure produced by the stroke of the pump in the right ventricle is a predetermined fraction of the maximum pressure produced by said stroke in the left ventricle of the artificial heart.

3. The pump of claim 1, wherein said separate chambers and respective pistons are substantially equal in cross-section and one of said chambers is greater in length such that said maximum pressure produced by the stroke of the pump in the right ventricle is a predetermined fraction of the maximum pressure produced by said stroke in the left ventricle of the artificial heart.

4. The pump of claim 1, wherein said separate chambers are substantially equal in length and one of said chambers and a respective piston are greater in cross-section such that said maximum pressure produced by the stroke of the pump in the right ventricle is a predetermined fraction of the maximum pressure produced by said stroke in the left ventricle of the artificial heart.

5. The pump of claim 1, further comprising a buffer chamber connected to one of said separate chambers such that said maximum pressure produced by the stroke of the pump in the right ventricle is a predetermined fraction of the maximum pressure produced by said stroke in the left ventricle of the artificial heart.

6. The pump of claim 1, further comprising an actuator for producing reciprocating motion of said pistons in the separate chambers.

7. The pump of claim 1, further comprising a pressure limiting valve and a vacuum limiting valve in each of said chambers.

8. The pump of claim 1, wherein said housing, pistons and connector have a circular cross-section.

9. The pump of claim 8, wherein said pistons have a diameter of approximately 3.0 inches and a stroke length of about 0.943 inches, and said connector has a diameter of 1.1 inches.

10. A pneumatically driven artificial heart comprising:

a right ventricle and a left ventricle implanted on a human heart, each comprising a diaphragm actuated by pneumatic pressure;
an exterior housing;
a pair of pistons slidably mounted inside the housing;
a partition defining two separate chambers in the housing, each chamber containing one of said pistons;
a connector coupling said pair of pistons through the partition; and
a pair of air lines connecting said chambers to respective ventricles of the artificial heart;
wherein said separate chambers are adapted to produce respective displacements such that a maximum pressure produced by a stroke of the pump in the right ventricle is a predetermined fraction of a maximum pressure produced by said stroke in the left ventricle of the artificial heart.

11. The pneumatically driven artificial heart of claim 10, wherein said separate chambers and respective pistons are substantially equal in cross-section and said connector is sized such that said maximum pressure produced by the stroke of the pump in the right ventricle is a predetermined fraction of the maximum pressure produced by said stroke in the left ventricle of the artificial heart.

12. The pneumatically driven artificial heart of claim 10, wherein said separate chambers and respective pistons are substantially equal in cross-section and one of said chambers is greater in length such that said maximum pressure produced by the stroke of the pump in the right ventricle is a predetermined fraction of the maximum pressure produced by said stroke in the left ventricle of the artificial heart.

13. The pneumatically driven artificial heart of claim 10, wherein said separate chambers are substantially equal in length and one of said chambers and a respective piston are greater in cross-section such that said maximum pressure produced by the stroke of the pump in the right ventricle is a predetermined fraction of the maximum pressure produced by said stroke in the left ventricle of the artificial heart.

14. The pneumatically driven artificial heart of claim 10, further comprising a buffer chamber connected to one of said separate chambers such that said maximum pressure produced by the stroke of the pump in the right ventricle is a predetermined fraction of the maximum pressure produced by said stroke in the left ventricle of the artificial heart.

15. The pneumatically driven artificial heart of claim 10, wherein said air lines connecting said chambers to respective ventricles of the artificial heart are sized such that said maximum pressure produced by the stroke of the pump in the right ventricle is a predetermined fraction of the maximum pressure produced by said stroke in the left ventricle of the artificial heart.

16. The pneumatically driven artificial heart of claim 10, further comprising an actuator for producing reciprocating motion of said pistons in the separate chambers.

17. The pneumatically driven artificial heart of claim 10, wherein said housing, pistons and connector have a circular cross-section.

18. The pneumatically driven artificial heart of claim 17, wherein said pistons have a diameter of approximately 3.0 inches and a stroke length of about 0.943 inches, and said connector has a diameter of 1.1 inches.

19. A pump for driving an artificial heart comprising a right ventricle and a left ventricle actuated by pneumatic pressure, comprising:
- a housing of circular cross-section;
- a pair of pistons slidably mounted inside the housing;
- a partition defining two separate cylindrical chambers in the housing, each chamber containing one of said pistons;
- a tubular connector coupling said pair of pistons through the partition;
- a port connecting each of said chambers to a respective ventricle of the artificial heart;
- a pressure limiting valve in each of said chambers;
- a vacuum limiting valve in each of said chambers; and
- an actuator for producing reciprocating motion of said pistons in the separate chambers;
- wherein said pistons have a diameter of approximately 3.0 inches and a stroke length of about 0.943 inches, and said connector has a diameter of 1.1 inches, such that a maximum pressure produced by a stroke of the pump in the right ventricle is a predetermined fraction of a maximum pressure produced by said stroke in the left ventricle of the artificial heart.

\* \* \* \* \*